(12) United States Patent
Almoazen (10) Patent No.: US 11,021,437 B2
(45) Date of Patent: Jun. 1, 2021

(54) PHARMACEUTICAL FORMULATION FOR SUBLINGUAL OR BUCCAL DELIVERY OF EPINEPHRINE OR A PRO-DRUG THEREOF

(71) Applicant: Iono Pharma, LLC, Bartlett, TN (US)

(72) Inventor: Hassan Almoazen, Bartlett, TN (US)

(73) Assignee: IONO Pharma, LLC, Bartlett, TN (US)

( * ) Notice: Subject to any disclaimer, the term of this patent is extended or adjusted under 35 U.S.C. 154(b) by 120 days.

(21) Appl. No.: 16/347,625

(22) PCT Filed: Nov. 9, 2017

(86) PCT No.: PCT/US2017/060761
§ 371 (c)(1),
(2) Date: May 6, 2019

(87) PCT Pub. No.: WO2018/089570
PCT Pub. Date: May 17, 2018

(65) Prior Publication Data
US 2019/0337886 A1    Nov. 7, 2019

Related U.S. Application Data

(60) Provisional application No. 62/421,316, filed on Nov. 13, 2016.

(51) Int. Cl.
| | | |
|---|---|---|
| C07C 219/30 | (2006.01) |
| A61K 9/00 | (2006.01) |
| A61K 47/02 | (2006.01) |
| A61K 47/10 | (2017.01) |
| A61K 47/12 | (2006.01) |
| A61K 47/26 | (2006.01) |
| A61K 47/46 | (2006.01) |
| A61K 31/137 | (2006.01) |

(52) U.S. Cl.
CPC ............ *C07C 219/30* (2013.01); *A61K 9/006* (2013.01); *A61K 47/02* (2013.01); *A61K 47/10* (2013.01); *A61K 47/12* (2013.01); *A61K 47/26* (2013.01); *A61K 47/46* (2013.01); *A61K 31/137* (2013.01)

(58) Field of Classification Search
CPC combination set(s) only.
See application file for complete search history.

(56) References Cited

U.S. PATENT DOCUMENTS

| | | | |
|---|---|---|---|
| 3,809,714 A | 5/1974 | Hussain et al. |
| 3,825,583 A | 7/1974 | Hussain et al. |
| 4,136,145 A | 1/1979 | Fuchs et al. |
| 4,145,441 A | 3/1979 | Bodor |
| 4,320,144 A | 3/1982 | Resnick |
| 2003/0180357 A1 | 9/2003 | Martino et al. |
| 2007/0202163 A1 | 8/2007 | Rawas-Qalaji et al. |
| 2019/0022023 A1 | 1/2019 | Schobel et al. |

OTHER PUBLICATIONS

Arya, A. et. al., "Fast dissolving oral films: An innovative drug delivery system and dosage form," Int. J. ChemTech Res., vol. 2, No. 1. pp. 576-583, 2010.
Hussain, A, Journal of Pharmaceutical Sciences, vol. 65, No. 10, Oct. 1976, p. 1510-1512.
International Preliminary Report on Patentability PCT/US2017/060761 dated Nov. 2, 2018.
International Search Report PCT/US2017/060761 dated Jan. 25, 2018.
Rawas-Qalaji, et al., Adrenaline (epinephrine) microcrystal sublingual tablet formulation: enhanced absorption in a preclinical model, J of Pharmacy and Pharmacology, 67,pp. 20-25 (2014).
Rawas-Qalaji, M. et. al, Sublingual epinephrine tablets versus intramuscular injection of epinephrine:Dose equivalence for potential treatment of anaphylaxis. J of Allergy Clin Immunol, v 117 No. 2, 398 (2006).
Singh, S. et. al. "Formulation and Evaluation of Rapidly Disintegrating Film of Levocetrizine Hydrochloride," Pharmacia, vol. 2, No. 2, pp. 208-220, 2010.

*Primary Examiner* — Kortney L. Klinkel
*Assistant Examiner* — Tori Strong
(74) *Attorney, Agent, or Firm* — Veritay Group IP PLLC; Susan B. Fentress (57) ABSTRACT

The present invention relates to a pharmaceutical composition for the treatment of anaphylaxis formulated for rapid delivery, in one embodiment, the delivery vehicle is a rapidly dissolving film. The films contain an epinephrine or a novel epinephrine pro-drag for fee rapid treatment of anaphylaxis in a patient. This invention relates to pharmaceutical compositions made by modifying the physicochemical properties of epinephrine in order to enhance its permeability through biological membranes (sublingual and buccal membranes). Several prodrugs of epinephrine are shown by modifying the two hydroxyl (phenolic) groups in positions 3 and 4 on the benzene ring, by chemically reacting the two groups with several acid moieties to form an ester bond with different alkyl chains. The addition of an alkyl group will enhance the lipophilicity of epinephrine (increase log P) and will consequently increase its permeability through the biological membranes (sublingual and buccal tissues in the oral cavity).

5 Claims, 9 Drawing Sheets

3C 4-(1-hydroxy-2-(methylamino)ethyl)-1,2-phenylene bis(2,2-dichloroacetate)
CLogP: 1.4494

R4=Cl
R4=I

D

3D

4-(1-hydroxy-2-(methylamino)ethyl)-1,2-phenylene bis(2,2,2-trichloroacetate)
CLogP: 2.8554

4E 4-(1-hydroxy-2-(methylamino)ethyl)-1,2-phenylene bis(2,3-dimethylbutanoate)
CLogP: 2.6294

R2=CH3
R2=Cl
R2=I

F

4F

4-(1-hydroxy-2-(methylamino)ethyl)-1,2-phenylene bis(2,2,3-trimethylbutanoate)
CLogP: 3.4274

G 4-(1-hydroxy-2-(methylamino)ethyl)-1,2-phenylene dicarboniodidate
CLogP: 1.0854

4-(1-hydroxy-2-(methylamino)ethyl)-1,2-phenylene bis(2-iodoacetate)
CLogP: 0.3834

4-(1-hydroxy-2-(methylamino)ethyl)-1,2-phenylene dibutyrate
CLogP: 1.2134

FIG. 6

H 4-(1-hydroxy-2-(methylamino)ethyl)-1,2-phenylene (2E,2E)-bis(but-2-enoate)
CLogP: 1.2054

I 4-(1-hydroxy-2-(methylamino)ethyl)-1,2-phenylene bis(2-methylbutanoate)
CLogP: 1.8314

FIG. 7

4-[1-hydroxy-2-(methylamino)ethyl]-1,2-phenylene diacetate
CLogP: -0.9028

4-[1-hydroxy-2-(methylamino)ethyl]-1,2-phenylene bis(2-methylpropanoate)
CLogP: 0.7733

4-[1-hydroxy-2-(methylamino)ethyl]-1,2-phenylene dipropanoate
CLogP: 0.1554

4-[1-hydroxy-2-(methylamino)ethyl]-1,2-phenylene bis(2,2-dimethylpropanoate)
CLogP: 1.5714

FIG. 8

PHARMACEUTICAL FORMULATION FOR SUBLINGUAL OR BUCCAL DELIVERY OF EPINEPHRINE OR A PRO-DRUG THEREOF

CROSS REFERENCE TO RELATED APPLICATIONS

This application is a § 371 National Stage Application of PCT/US517/60761 application filed 9 Nov. 2017 and U.S. provisional patent application Ser. No. 62/421,316 filed 13 Nov. 2016, under 35 U.S.C. § 111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DSC APPENDIX

None.

FIELD OF THE INVENTION

The present invention relates to pharmaceutical compositions for the treatment of anaphylaxis formulated for rapid sublingual or buccal delivery, i.e., compounds that dissolves in the oral cavity. In one embodiment, the delivery vehicle is a rapidly dissolving film. The films contain an epinephrine, or a novel epinephrine pro-drug formulated for the rapid delivery of the drug to a patient in need of treatment, such as for example, a patient in need of treatment for anaphylaxis.

DESCRIPTION OF RELATED ART INCLUDING INFORMATION

Epinephrine is considered the primary choice for the treatment of anaphylaxis which is a life threatening allergic reaction that might lead to death if untreated especially in children. A study reported that one in every 10,000 children has an anaphylactic attack per year. Epinephrine is the drug of choice for the treatment of anaphylactic shock in children and adults. It is highly soluble in water, highly hydrophilic (log P–0.68) and can be oxidized readily. Based on the current physicochemical properties of epinephrine, the only delivery available in the market is intramuscular injection. The administration of proper therapeutic agents, such as, epinephrine must be prompt. This is usually performed through the usage of auto-injectors such as EPIPEN (MLAN) air TWINJECT (SHIONOGI PHARMA, INC.) that deliver the required dose in the mid-outer thigh either subcutaneously or intramuscularly. However, many disadvantages are reported with the usage of these injectors such as high cost, inaccurate administration, short half-life, patient's fear of needles, accidental injections, and unavailability of a sufficient number of fixed prefilled doses.

These shortcomings affect greatly the patient compliance and adherence to these injectors. In addition, it is very challenging to adjust the dose to different children ages as there are only two premeasured fixed epinephrine doses (0.15 and 0.3 mg). Recent study showed that only 17% of pediatric patients who have experienced anaphylactic symptoms have used prescribed auto injectors. Other available delivery systems such as syringes or inhalers are also underused due to their lack of rapid and accurate dosing. Therefore, there is growing interest in the development of an alternative non-invasive delivery system that can easily provide accurate doses of epinephrine.

Figure 7:
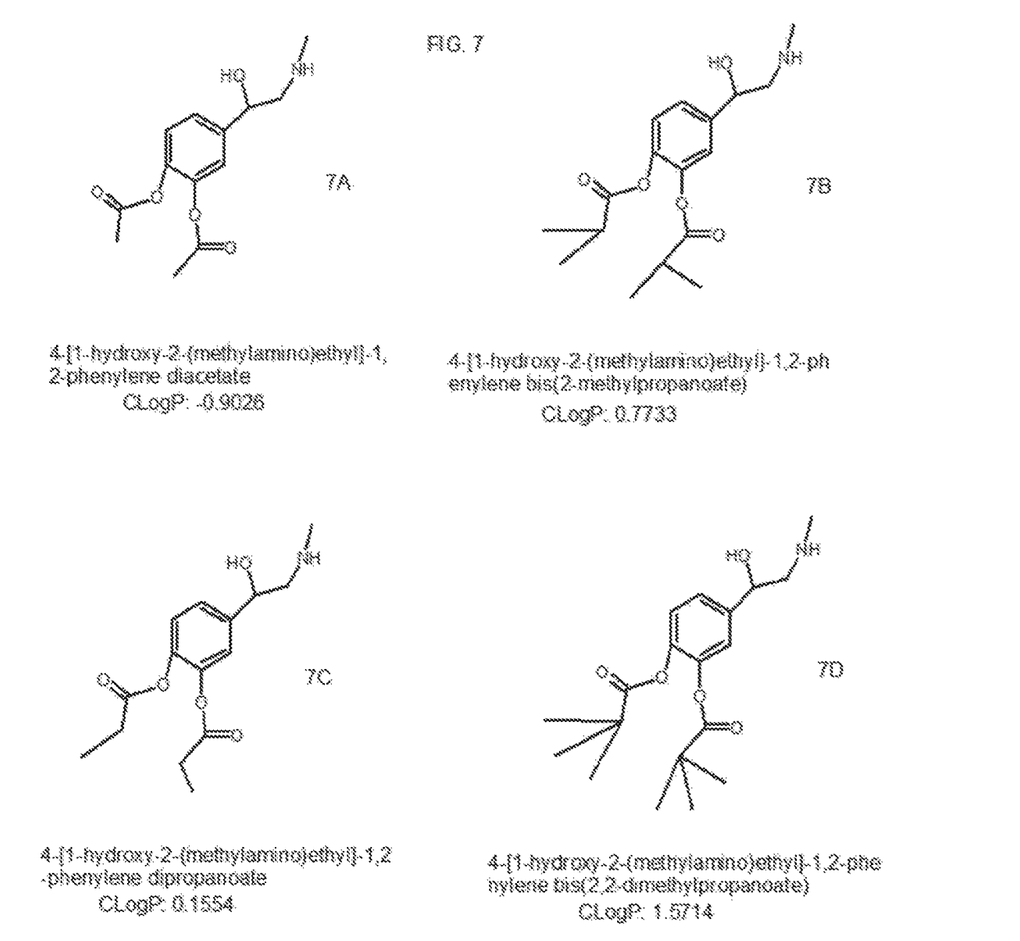
FIG. 7 shows Anwar A. Hussain and James E. Truelove compounds.

Anwar A. Hussain and James B. Truelove were granted patents related to the synthesis of novel esters of [(methylamino)methyl] benzyl alcohol which is epinephrine. The purpose of the Hussain's et. al. invention was to develop a prodrug of epinephrine HCl with superior lipid solubility to enhance penetration through the cornea of the eye to treat glaucoma. Hussain et. al. synthesized four different prodrugs for this purpose (see structures 7A, 7B, 7C, 7D). These four molecules were tested in human, rabbit and horse plasmas and found that 3,4-dipivalyl-α-[(methylamino) methyl] benzyl alcohol hydrochloride (structure 7D) shows the best penetration profile into the eye. Hussain's et. al. didn't evaluate the log P of these molecules nor did they evaluate the sublingual or buccal permeability or absorption. Their main focus was to develop a prodrug specifically for the eye. Since the initial publishing of Anwar's patents in 1974 and 1975, no one has followed up or even published any new data on structures 7A, 7B, and 7C. Dipivalyl-α-[(methylamino)] benzyl alcohol hydrochloride (7D) was further developed into a drug delivery system for glaucoma (Dipivefrin or Propine). Hussain and Truelove selected this prodrug for further development because of several physicochemical and biological qualities. The first quality was estimating the delay before onset of seizure for this prodrug was about 8-10 minutes, the second quality was the rate of hydrolysis expressed as $t_{1/2}$ in human plasma was about 1,800 seconds and the third quality was the $t_{1/2}$ hydrolysis and oxidation in vitro was 700 and 300 days respectively. In a separate publication (Journal of Pharmaceutical Sciences, Vol. 65, No. 10, October 1976, p: 1510-1512), Hussain et. al. shared the graphs for the in vitro hydrolysis of this particular prodrug using rabbit eye homogenate and compared the hydrolysis among three different plasmas (human, rabbit, rabbit eye homogenate).

Films that incorporate a pharmaceutically active ingredient are disclosed in U.S. Pat. No. 4,136,145 to Fuchs, et al. ("Fuchs"). These films can be formed into a sheet, dried and then cut into individual doses. Examples of specific uses disclosed by Fuchs include application of the films to mucosal membrane areas of the body, including the mouth, rectal, vaginal, nasal and ear areas. A drug delivery vehicle must provide a high level of uniformity with respect to the dosage delivered.

BRIEF SUMMARY OF THE INVENTION

This invention relates to pharmaceutical compositions made by modifying the physicochemical properties of epinephrine in order to enhance its permeability through biological membranes (sublingual and buccal membranes). Several prodrugs of epinephrine are shown by modifying the two hydroxyl (phenolic) groups in positions 3 and 4 on the benzene ring, by chemically reacting the two groups with several acid moieties to form an ester bond with different alkyl chains. The addition of an alkyl group will enhance the lipophilicity of epinephrine (increase log P) and will consequently increase its permeability through the biological membranes (sublingual and buccal tissues in the oral cavity). The 3 and 4 positions represent meta and para locations with respect to the carbon in position 1 on the phenolic ring of epinephrine. Once the prodrug penetrates biological membranes (sublingual and buccal), the biological enzyme carboxyesterase will degrade the ester bond and release epinephrine for therapeutic activity. A prodrug is a biologically inactive compound that can be metabolized in the body to produce a drug. On characteristic of the selected prodrug compounds is fast hydrolysis in plasma.

In another embodiment, the subject matter includes a method to deliver epinephrine involving the steps of: providing epinephrine in a unit dosage form formulated for sublingual or buccal administration, wherein the unit dosage form is a rapidly dissolving film and the unit dosage form provides the pharmaceutical pro-drug of epinephrine. More specifically, this method involves providing pharmaceutical pro-drug compositions epinephrine in a unit dosage form to patients in need of anaphylactic treatment.

The subject matter includes a pharmaceutical formulation made of: a compound as depicted in a formula 2A and a pharmaceutically acceptable carrier or a pharmaceutically acceptable excipient, wherein $R_1$ is selected for the group consisting of $CH_3$, CL and I. A pharmaceutical formulation made of: a compound as depicted in a formula 2B and a pharmaceutically acceptable carrier or a pharmaceutically acceptable excipient, wherein $R_3$ is selected for the group consisting of: CL and I. A pharmaceutical formulation made of: a compound as depicted in a formula 3C and a pharmaceutically acceptable carrier or a pharmaceutically acceptable excipient, wherein $R_4$ is selected for the group consisting of CL and I. A pharmaceutical formulation made of a compound as depicted in a formula 3D and a pharmaceutically acceptable carrier or a pharmaceutically acceptable excipient, wherein $R_1$ is selected for the group consisting of: $CH_3$, CI and I. A pharmaceutical formulation made of: a compound as depicted in a formula 4E and a pharmaceutically acceptable carrier or a pharmaceutically acceptable excipient, wherein $R_2$ is selected for the group consisting of $CH_3$, CI and I. A pharmaceutical formulation made of: a compound as depicted in a formula 4F and a pharmaceutically acceptable carrier or a pharmaceutically acceptable excipient, wherein $R_1$ is selected for the group consisting of: $CH_3$, CI and I. A pharmaceutical formulation made of: a compound as depicted in a formula 5G and a pharmaceutically acceptable carrier or a pharmaceutically acceptable excipient, wherein $R_1$ is selected for the group consisting of: H, I, CI, $CH_2CH_2CH_3$ & $CH_2CH_2CH_2CH_3$, $CH_2CI$, $CH_2I$ and $CH_2F$ A pharmaceutical formulation made of a compound as depicted in a formula 6H and a pharmaceutically acceptable carrier or a pharmaceutically acceptable excipient, wherein $R_2$ is selected for the group consisting of: H, $CH_3$, CI and I. A pharmaceutical formulation made of a compound as depicted in a formula 6I and a pharmaceutically acceptable carrier or a pharmaceutically acceptable excipient, wherein $R_3$ is selected for the group consisting of CI, I and $CH_3$. The compound is formulated in a unit dosage form as a rapidly dissolving film. The invention further provides use of the pharmaceutical formulation in a patient in need of anaphylactic treatment.

BRIEF DESCRIPTION OF SEVERAL VIEWS OF THE DRAWING(S)

The invention can be best understood by those having ordinary skill in the art by reference to the following detailed description when considered in conjunction with the accompanying drawings in which.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about." it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms used herein have the same meaning as commonly understood by one of ordinary skill in the art to which this invention belongs. Reference will now be made in detail to the presently preferred embodiments of the invention, examples of which are illustrated in the accompanying drawings. Throughout the following detailed description, the same reference numerals refer to the same elements in all figures.

Figure 1:
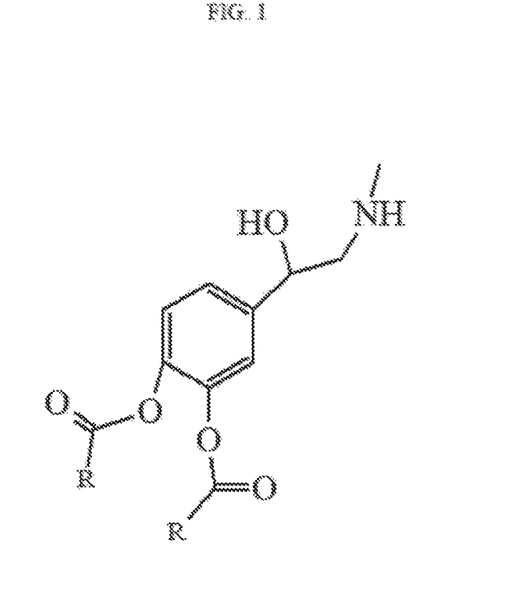
FIG. 1 shows the generic chemical structure of a biologically inactive compound of this invention.

The present invention provides a novel biologically inactive compound trial can be metabolized in the body to produce a drug that has the biological activity of epinephrine. Epinephrine acts on nearly all body tissues. Its actions vary by tissue type and tissue expression of adrenergic receptors. For example, high levels of epinephrine cause smooth muscle relaxation in the airways but cause contraction of the smooth muscle that lines most arterioles. The present subject matter relates to modifying the physicochemical properties of epinephrine in order to enhance its permeability through biological membranes (sublingual and buccal membranes. FIG. 1 shows the generic chemical structure of a biologically inactive compound of this invention, while Table 1 shows exemplary prodrugs of epinephrine made by modifying the two hydroxyl (phenolic) groups in positions 3 and 4 on the benzene ring along with Log P values or a pharmaceutically acceptable salt thereof. The prodrugs of epinephrine preferably have a Log P value in the range of about 0.5-6.0, and more preferably between 1.0-5.0. This range was listed as a table of marketed sublingual tablets and films in Ashraf et. al "Considerations in developing sublingual tablets—An overview", Pharmaceutical Technology, 2014, 38(11). Log P is the logarithmic value of the ratio of two concentrations of a compound in a mixture of two immiscible liquids such as water and octanol at equilibrium Log P values can be calculated mathematically by the use of PERCEPTA PLATFORM software (ACS Labs, Toronto, Ontario, Canada).

TABLE 1

| R | Log P | R | Log P |
|---|---|---|---|
| R=CHCH$_2$ | −0.20 | R=CH$_2$COCH$_3$ | −1.44 |
| R=CHCHCH$_3$ | +0.84 | R=CH$_2$COCL | −0.21 |
| R=CHCH$_2$CL | +0.05 | R=CH$_2$COI | +1.10 |
| R=CHCH$_2$I | +1.36 | R=CH$_2$OCH$_3$ | −1.29 |
| R=CHCLCH$_2$CL | +0.78 | R=CHICH$_3$ | +1.82 |
| R=CHICH$_2$I | +4.0 | R=CCLCLCH$_3$ | +1.36 |
| R=CHCH$_2$CH$_2$CH$_3$ | +1.85 | R=CH$_2$CHCH$_3$CH$_3$ | +1.85 |
| R=CH$_2$CCH$_3$CH$_3$CH$_3$ | +2.55 | R=CH$_2$CHCLCL | +1.06 |
| R=CH$_2$CH$_2$CH$_3$ | +0.8 | R=CH$_2$CHII | +4.09 |
| R=CH$_2$CL | −0.51 | R=CH$_2$CCLCLCL | +2.97 |
| R=CH$_2$I | +1.12 | R=CH$_2$CIII | +7.68 |
| R=CH$_2$F | −0.85 | R=CHCLCL | +0.66 |
| R=CIII | +8.13 | R=CHII | +4.03 |
| R=CL | +1.24 | R=CCH$_3$CH$_3$CHCH$_3$CH$_3$ | +3.24 |
| R=I | +2.55 | R NHCCH$_3$CH$_3$CH$_3$ | +1.63 |
| R=F | +0.72 | R=NHCHCH$_3$CH$_3$ | +1.28 |
| R=CHCH$_3$CHCH$_3$CH$_3$ | +2.54 | R=NHCH$_2$CH$_3$ | +0.93 |
| R=CHCLCHCLCL | +2.08 | R=NHCH$_3$ | +0.40 |
| R=CHICHII | +7.09 | R=SCH$_3$ | +1.92 |
| R=CHFCHFF | +0.80 | R=SCH$_2$CH$_3$ | +2.45 |
| R=CH$_2$CHCH$_2$ | +0.07 | R=SCHCH$_2$CH$_3$ | +2.80 |
| R=CCLCLCHCLCL | +4.18 | R=SCCH$_3$CH$_3$CH$_3$ | +3.15 |
| R=CIICHII | +11.29 | R=CH$_2$C$_6$H$_5$ | +2.52 |
| R=CCLCLCL | +2.90 | R=C$_6$H$_5$ | +3.10 |

Figure 2:
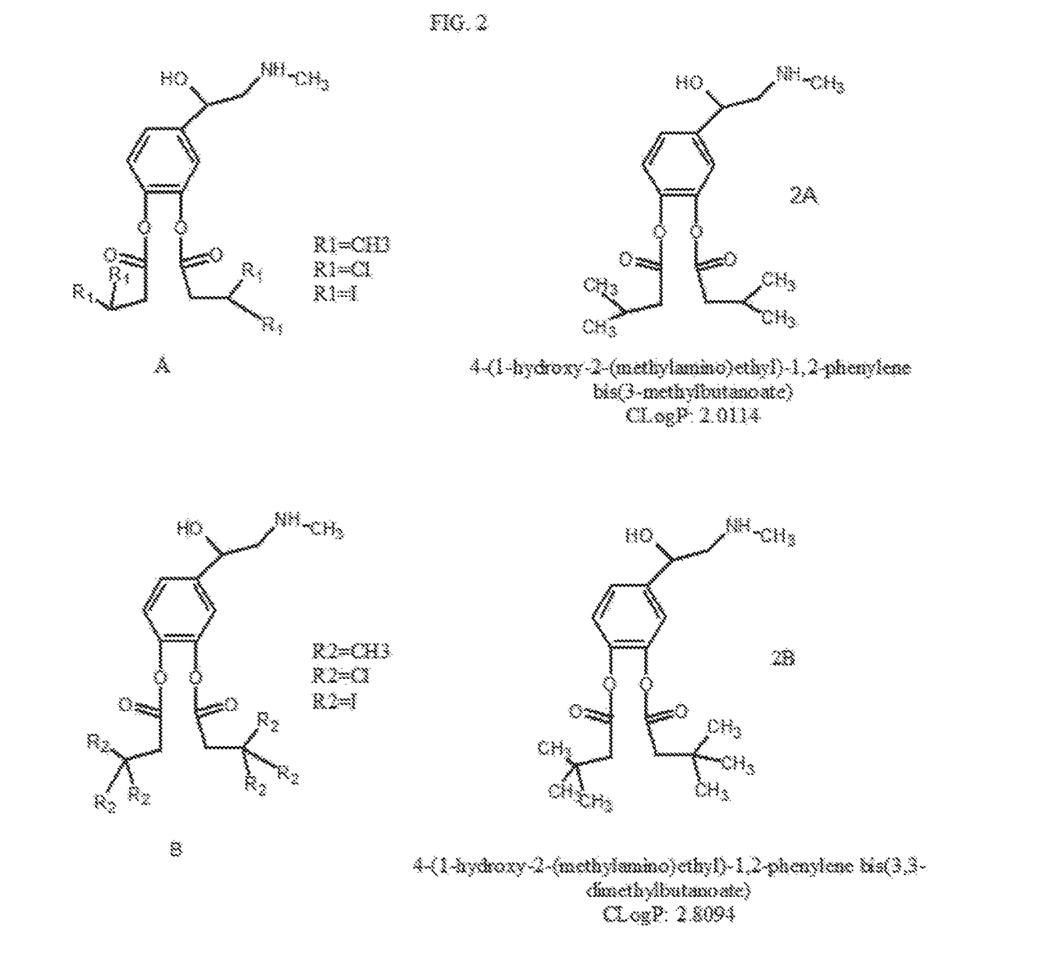
FIG. 2 shows exemplary compounds of the present invention.
Figure 3:
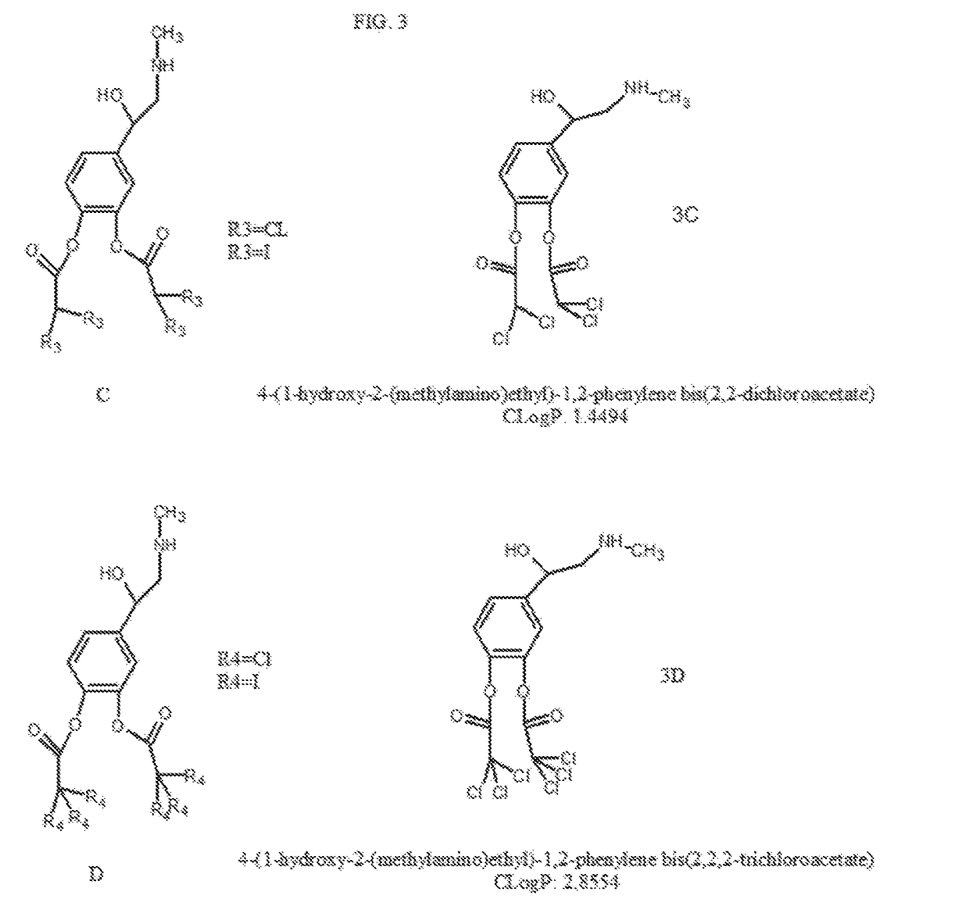
FIG. 3 shows exemplary compounds of the present invention.

A pro-drug is a derivative of epinephrine selected for fast permeability through sublingual and buccal membranes (ie a compound that dissolves in the oral cavity) and fast hydrolysis (half-life $t_{1/2}$ range from 1-6 minutes) by plasma enzymes to form epinephrine when delivered. These characteristics are physical properties of a compound that is useful to be formulated in a unit dosage form as a rapidly dissolving film. Now referring to FIG. 2, derivatives of epinephrine are shown. Structure 2A represents di-ester derivatives of epinephrine where the R$_1$ can be a short alkyl chain of CH$_3$, CH$_2$CH$_3$, CH$_2$CH$_2$CH$_3$, or CH$_2$CH$_2$CH$_2$CH$_3$, CL or I. A representative molecule of this group compounds is: 4-(1-hydroxy-2-(methylamino)ethyl)-1,2-phenylene bis (3-methylbutanoate) having a C Log P: 2.0114. Structure 2B represents derivatives of epinephrine where R$_2$=CH$_3$, CL or I. A representative molecule of this group of compounds is 4-(1-hydroxy-2-(methylamino) ethyl)-1,2-phenylene bis(3, 3-dimethylbutanoate) having a C Log P: 2.8094. Adding H, CH$_3$, Cl or I change the Log P of the prodrug and adds a non-toxic moiety to the molecule. The rate of hydrolysis of each ester can increase or decrease depending on how the atom in position R$_4$ influences the ester group Now referring to FIG. 3, derivatives of epinephrine are shown. Structure 3C represents a derivative of epinephrine where R$_3$=Cl or I. A representative molecule of the group is: 4-(1-hydroxy-2-(methylamino)ethyl)-1,2-phenylene bis (2,2-dichloroacetate) having a C Log P: 1.4494. Structure 3D represents a derivative of epinephrine where R$_4$=Cl or I. A representative molecule of the groups is: 4-(1-hydroxy-2-(methylamino)ethyl)-1,2-phenylene bis(2,2,2-trichloroacetate) having a C Log P: 2.8554. The molecule that shows fast permeability through the sublingual and buccal membranes and fast hydrolysis by the enzyme is a physical property of a compound that is useful to be formulated in a unit dosage form as a rapidly dissolving film.

Figure 4:
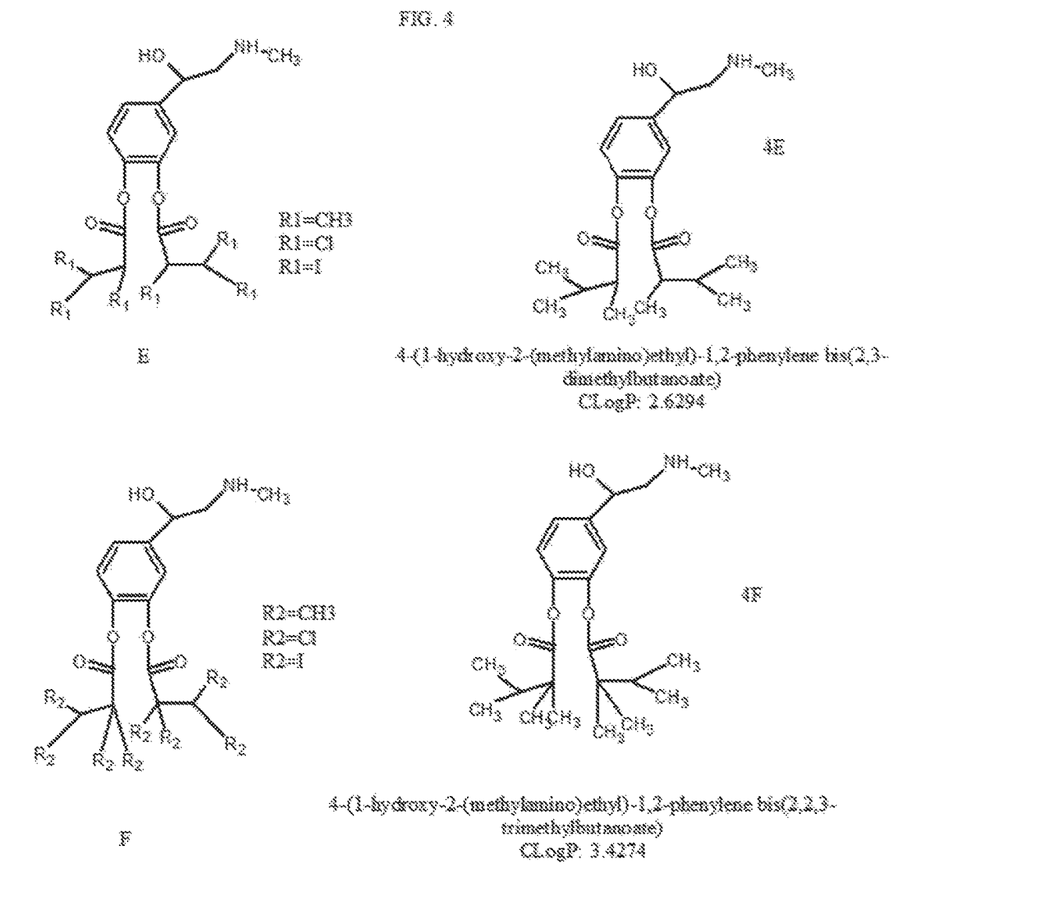
FIG. 4 shows exemplary compounds of the present invention.

Now referring to FIG. 4 derivatives of epinephrine are shown. Structure 4E represents a derivative of epinephrine where R1=CH3, CL or I. A representative molecule is: 4-(1-hydroxy-2-(methylamino)ethyl)-1,2-phenylene bis(2, 3-dimethylbutanoate) having a C Log P: 2.6294, Structure 4F represents a derivative of epinephrine where R$_2$=CH$_3$, CL or I. A representative molecule is: 4-(1-hydroxy-2-(methylamino)ethyl)-1,2-phenylene bis(2,2,3-trimethylbutanoate) having a C Log P: 3.4274. The molecule that shows fast permeability through the sublingual and buccal membranes and fast hydrolysis by the enzyme is a physical property of a compound that is useful to be formulated in a unit dosage form as a rapidly dissolving film.

Figure 5:
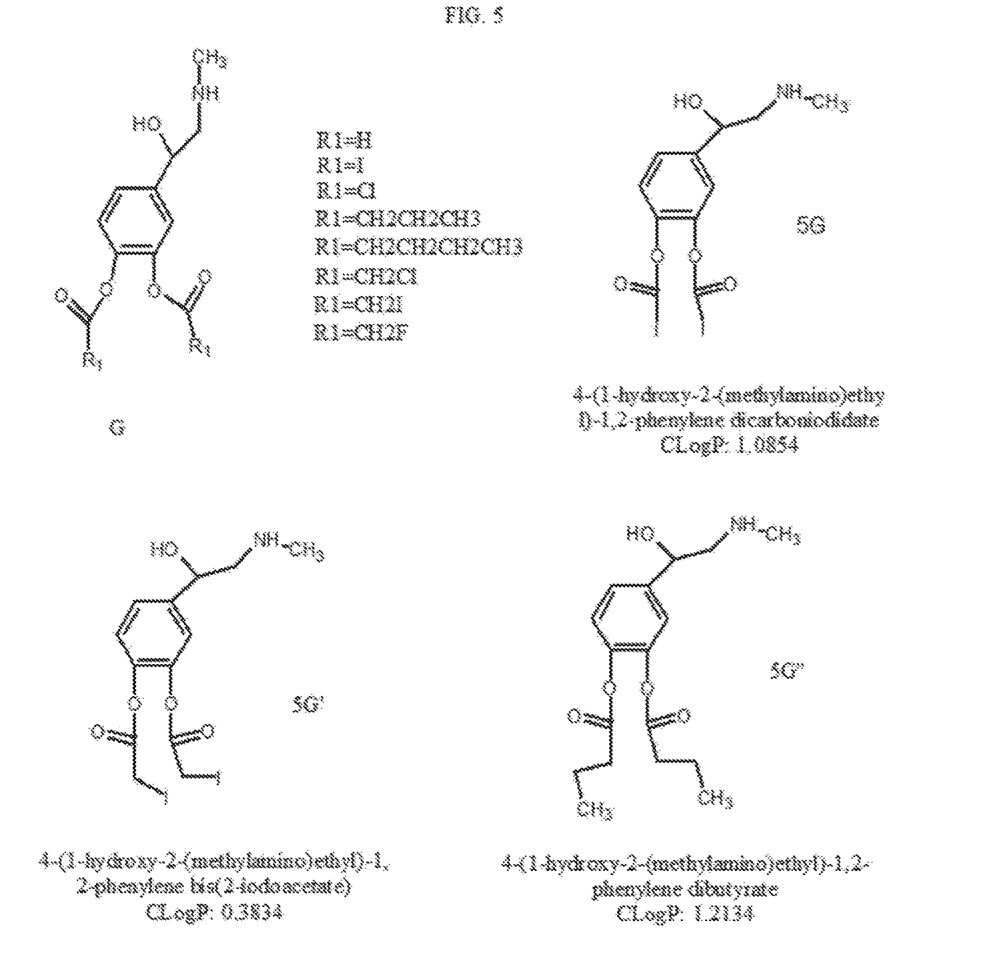
FIG. 5 shows exemplary compounds of the present invention.

Now referring to FIG. 5, derivatives of epinephrine are shown. Structure G represents a derivative epinephrine where R$_1$=H, I, Cl, CH$_2$CH$_2$CH$_3$ & CH$_2$CH$_2$CH$_2$CH$_3$, CH$_2$CI, CH$_2$I or CH$_2$F. Representative molecules are: 5G 4-(1-hydroxy-2-ethyl) 1,2-phenylene dicarboniodidate having a C log: 1.084; 5G' 4-(1-hydroxy-2-(methylamino-ethyl)-1,2-phenylene bis (2-iodoacetate) having a C Log P: 0.3834 and Structure 5G" 4-(1-hydroxy-2-methylamino) ethyl)-1,2-phenylene dibutyrate) having a C Log P: 1.2134.

Figure 6:
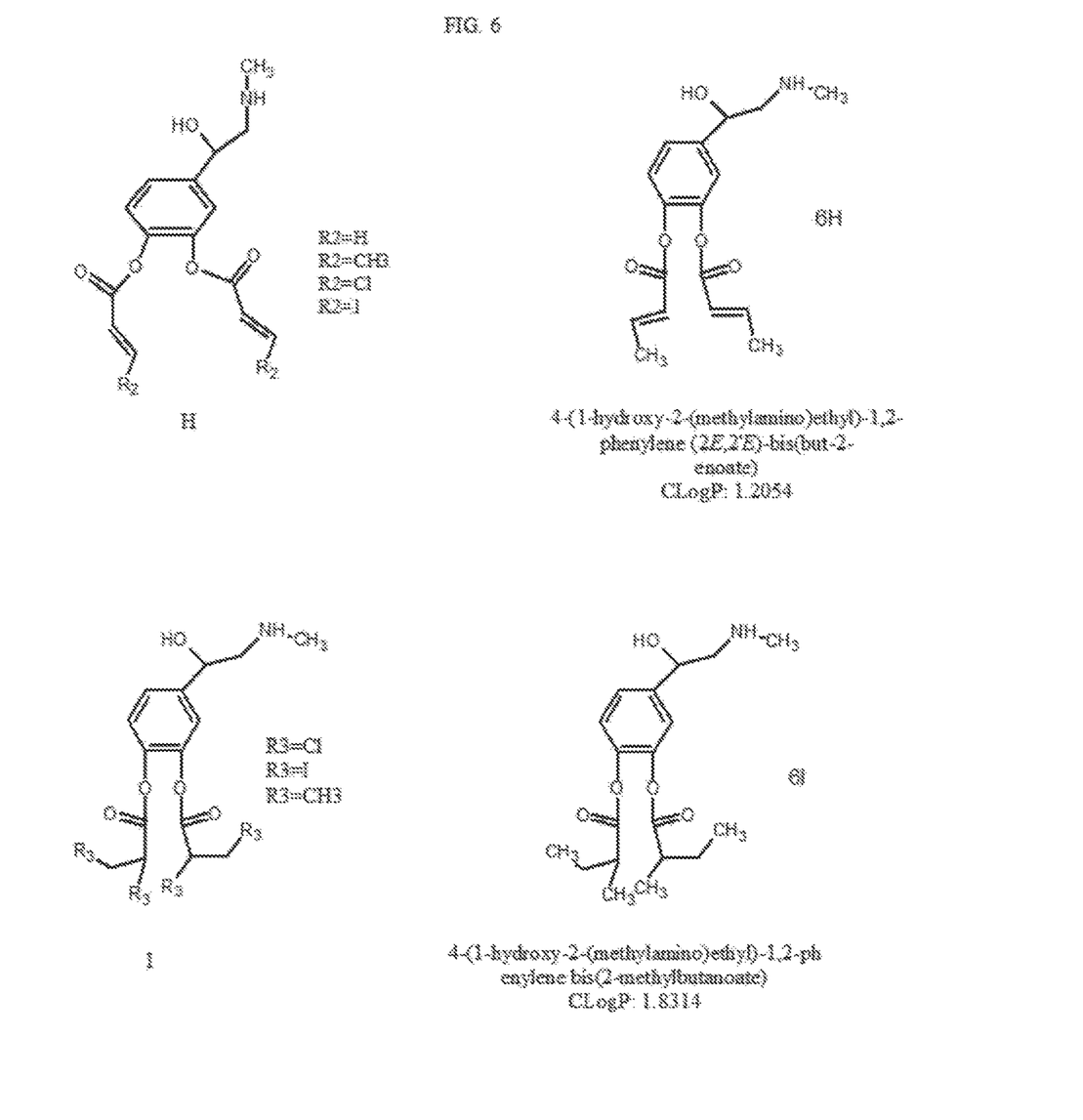
FIG. 6 shows exemplary compounds of the present invention.

Now referring to FIG. 6, a derivative epinephrine is shown, Structure H6 represents a derivative of epinephrine where R$_2$=H, CH$_3$, CL or I. A representative example is: 4-(1-hydroxy-2-(methylamino)ethyl)-1,2-phenylene (2E, 2'E)-bis(but-2-enoate) having a C Log P: 1.2054. Structure I6 represents a derivative of epinephrine where R$_3$=CL, I or CH$_3$. A representative example is: 4-(1-hydroxy-2-(methylamino)ethyl)-1,2-phenylene bis(2-methylbutanoate) having a C Log P: 1.8314.

Now referring to FIG. 7, the compounds of the invention as shown in U.S. Pat. Nos. 3,809,714 and 3,825,583 hereby incorporated by reference. Representative molecules include: 7A 4-(1-hydroxy-2-(methylamino)ethyl)-1,2-phenylene diacetate having a D Log P: −0.9026. 7B 4-(1-hydroxy-2(methylamino)ethyl)-1,2-phenylene bis(2-methylpropanoate) having a C Log P: 0.773300. 7C 4-(1-hydroxy-2-(methylamino)ethyl)-1,2-phenylene dipropionate having a C Log P: 0.1554. 7D 4-(1-hydroxy-2-(methylamino)ethyl)-1,2-phenylene bis(2,2-dimethylpropanoate) having a C Log P: 1.571.4. If these molecules show fast permeability through the sublingual and buccal membranes and fast hydrolysis by the enzyme (half-life 1-6 minutes) a physical property of a compound that is useful to be formulated in a unit dosage form as a rapidly dissolving film. The subject matter includes: uses of a pharmaceutical formulation in a patient in need of anaphylactic treatment, wherein the pharmaceutical formulation is made of a compound selected from the group consisting of 4-(1-hydroxy-2-(methylamino)ethyl)-1,2-phenylene diacetate; 4-(1-hydroxy-2(methylamino)ethyl)-1,2-phenylene bis(2-methylpropanoate); 4-(1-hydroxy-2-(methylamino)ethyl)-1, 2-phenylene dipropionate; 4-(1-hydroxy-2-(methylamino) ethyl)-1,2-phenylene bis(2,2-dimethylpropanoate), and a pharmaceutically acceptable carrier or a pharmaceutically acceptable excipient. A pharmaceutical formulation made of a compound selected from the group consisting of: 4-(1-hydroxy-2-(methylamino)ethyl)-1,2-phenylene di-acetate; 4-(1-hydroxy-2(methylamino)ethyl)-1,2-phenylene bis(2-methylpropanoate); 4-(1-hydroxy-2-(methylamino)ethyl)-1,2-phenylene dipropionate; 4-(1-hydroxy-2-(methylamino) ethyl)-1,2-phenylene bis(2,2-dimethylpropanoate), and a pharmaceutically acceptable carrier or a pharmaceutically acceptable excipient, wherein the compound is formulated in a unit dosage form as a rapidly dissolving film.

TABLE 2

| R | Log P |
|---|---|
| Structure 7A R=$CH_3$ | −0.97 |
| Structure 7C R=$CH_2CH_3$ | +0.09 |
| Structure 7B R=$CHCH_3CH_3$ | +0.79 |
| Structure 7D R=$CCH_3CH_3CH_3$ | +1.49 |

The present invention further provides a pharmaceutical composition made of at least one compound or mixture of compounds of the invention in a pharmaceutically acceptable carrier thereof. The invention features a pharmaceutical composition in unit dosage form formulated for sublingual or buccal administration. The delivery systems include: fast dissolving films, oral dissolving tablets, inhalation, and nasal delivery. In one embodiment, the unit dosage form of the present invention is a film for the delivery of epinephrine hydrochloride, as an anaphylactic treatment in a patient, such as for a pediatric or geriatric patient. A typical rapidly dissolving film is made of a drug, a water-soluble polymer, a plasticizer, a saliva stimulating agent, a surfactant and other fillers such as sweetening agents and flavors in case of bitter taste drugs. See e.g. A. Arya, A. Chandra, V. Sharma, and K. Pathak, "Fast dissolving oral films: An innovative drug delivery system and dosage form," *Int. ChemTech Res.*, vol. 2, no. 1, pp. 576-583, 2010. D. P. Lettre, "Formulation and Evaluation of Rapidly Disintegrating Film of Levocetrizine Hydrochloride," *Pharmacia*, vol. 2, no. 2, pp. 208-220, 2010.

For the present invention, the drug is epinephrine, a prodrug of epinephrine or a salt thereof. The typical dose of epinephrine for anaphylactic treatment is 0.3 to 0.5 mg in adults and 0.01 mg/kg up to a maximum of 0.3 mg in children administered through intramuscular route. In this study, 13 mg/9 $cm^2$ of epinephrine (5.9% w/w) are used as the dose size. This quantity is calculated for 6-7-year-old child according to Clark's rule Pediatric dose=Adult dose× (child's weight/150).

A typical dose of 40 mg was based on a study in rabbits that showed a dose bioequivalence between a 40 mg epinephrine tablet administered sublingually and 0.3 mg epinephrine administered intramuscularly using Epi pen. Injectors, Rawas-Qalaji et, al. Biopharm Drug Dispos. 27: 427-435 (2006). Furthermore, the time to reach maximum epinephrine concentration after a 0.3 mg EPIPEN (Mylan Specialty L.P.) injection in children is reported at 8±2 minutes. In another study, maximum plasma epinephrine concentration is reached within 34±14 minutes using 0.01 mg/kg dose injection of epinephrine subcutaneously in the deltoid region.

The polymer and the optimal amount of polymer are selected to obtain a non-sticky and functional film. A film-forming polymer should have good wetting property, high spread ability, good feeling in the mouth and should be safe and non-irritant. Many studies have showed that polymer content of at least 10-15% is needed in order to formulate proper film of proper thickness after drying in order to peel the film off from the release line. In one exemplary embodiment, the polymer is a water soluble modified hydroxy propyl starch that is specifically manufactured for aqueous film coating in immediate release solid oral dosage forms.

A plasticizer is used to form the rapidly dissolving film. The plasticizer enhances the flow of the polymer and improve the tensile strength and elongation of the fill. Several plasticizers are commonly used in rapidly dissolving film preparation such as glycerol, di-butylphthalate, and polyethylene glycols and they are usually used up to 20% concentration of dry polymer weight.

The function of the surfactant is to facilitate the solubilization or wetting of the film and subsequently causing the film to disintegrate quickly, releasing the drug to be absorbed through the buccal cavity. Surfactants can include Tween 80, which is a complex mixture of polyoxyethylene ethers used as emulsifiers or dispersing agents in pharmaceuticals.

A saliva stimulating agent used to facilitate the delivery of the drug using a rapidly dissolving film to the patient. Other fillers, such as sweetening agents and flavors in case of bitter taste drugs and colors are added to the rapidly dissolving film to facilitate the delivery of the drug using a rapidly dissolving film to the patient. Typically, acids such as citric acid, malic acid, lactic acid and ascorbic acid are used as chemical stimulants of saliva secretion. However, citric acid is the most preferred among them. Xylitol and Tutti Frutti flavor are used for taste masking. Xylitol is an effective sweetening agent which has equal sweetness to sucrose.

Examples: Four formulations are prepared in this example. Epinephrine is soluble in Lycoat 720 (modified hydroxypropyl starch) water mixture. This hydrophilic polymer solubilizes epinephrine HCl, form a high viscosity gel that spreads well as we cast the film and lead to a non-sticky dry film after water evaporation. This polymer doesn't have any oxyethylene groups that can promote the oxidation of epinephrine nor it has glucose units that promotes water adsorption. The other ingredients added such as tween, glycerin decreased the rigidity of the film and improved elasticity, sodium metabisulfite was added to prevent and long-term oxidation of epinephrine HCl in the film. The citric acid brings the oil of the gel to the maximum stability range for epinephrine. The percentages of the polymer are shown in (Table 3). The polymer percentages are (20, 25, 27 and 30%) of the total formulation weights. The polymer used in this example is LYCOAT (Ferromet). LYCOAT is a water soluble modified hydroxypropyl starch that is specifically manufactured for aqueous film coating in immediate release solid oral dosage forms.

TABLE 3

List of the cpmpositions of the four FDFs formulations

| Ingredient (% w/w) | Use | F1 | F2 | F3 | F4 |
|---|---|---|---|---|---|
| Epinephrine HCl | Drug | 5.9 | 5.9 | 5.9 | 5.9 |
| Sodium Metabisulfite | Antioxidant | 5.9 | 5.9 | 5.9 | 5.9 |
| Lycoat 720 (hrydratypropyl starch) | Film-forming polymer | 20 | 25 | 27 | 30 |
| Glycerin | Plasticizer | 3 | 3 | 3 | 3 |
| Tween 80 | Surfactant | 2 | 2 | 2 | 2 |
| Citric Acid Monohydrate | Buffer; increases absorption in oral cavity | 0.5 | 0.5 | 0.5 | 0.5 |

TABLE 3-continued

List of the compositions of the four FDFs formulations

| Ingredient (% w/w) | Use | F1 | F2 | F3 | F4 |
|---|---|---|---|---|---|
| Sodium Citrate Monobasic | Buffer | 0.5 | 0.5 | 0.5 | 0.5 |
| Xylitol | Sweetener | 10 | 10 | 10 | 10 |
| Tutti Fruiti | Flavor | 6 | 6 | 6 | 6 |
| Water |  | 46.2 | 41.2 | 39.2 | 36.2 |

Glycerin is used as a plasticizer to provide the proper elasticity for the film (Table 1). A plasticizer imparts a certain level of flexibility to the film by decreasing its brittleness. Films in this example are prepared using 3% glycerol which is equivalent to 10-15% of the amount of polymer used.

Tween 80 is used as a surfactant (Table 2). Citric acid is used to adjust the pH and can be used in rapidly dissolving film as a saliva simulating agent to increase the secretion rate of saliva which will further improve the disintegration time of the film. Finally, the addition of an antioxidant is very important for the stability of epinephrine. Prompt oxidation of epinephrine in aqueous solutions results in a colored inactive product which has been reported. Therefore, different types of antioxidants are used in the commercial injectors such as sodium metabisulfite, EDTA and ascorbic acid achieving shelf life of two years. In this exemplary embodiment, the addition of sodium metabisuflite stabilizes the film.

However, films formed by formulations 1, 2 and 3 are too sticky after drying rendering them unusable. Formulation 4, having 30% polymer content, formed a smooth, transparent, flexible and uniform film and therefore it is selected for further testing. The difference in stickiness is clearly related to the variation of the polymer content. This comes in agreement with a previous study that showed that using 22.5% of LYCOAT polymer formed a thin and flexible but sticky film at that concentration concluding that a higher percentage of polymer is needed.

Physical properties of the film prepared by formulation 4 are evaluated such as elastic modulus, thickness, content uniformity and dissolution time. Assessing these parameters is essential to determine the efficiency and usability of the film by patients. Elastic modulus is first studied as it represents a clear measure of the stiffness level of the film. It is calculated as the ratio of the applied stress over strain on a specific section.

Elastic's modulus=(Force at corresponding strain/ cross section area)×(corresponding strain).

Figure 8:
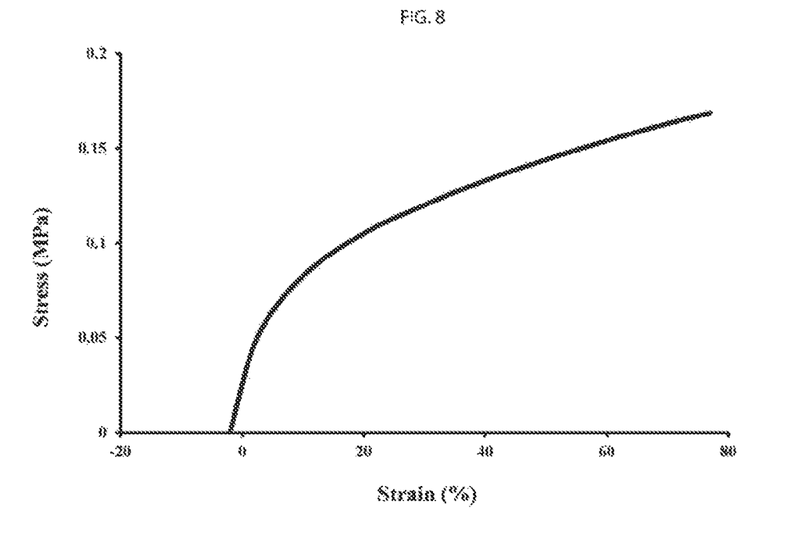
FIG. 8 shows a stress-strain profile of the optimized epinephrine fast dissolving film.

Now referring to FIG. 8, the profile of the film is illustrated showing a small increase in the applied strain to the film causes a quick increase in stress reaching a value of 0.1 MPa at 20% strain level. As the strain increases further above 20%, the increase magnitude in stress decreases gradually until it reaches a semi-plateau at value 0.16 MPa where % stress is 80%. The value of elastic modulus is determined at 1.325 MPa which is an indication of very good flexibility of the film (Table 3).

TABLE 4

List of physical properties of the optimized film

| Test | Results |
|---|---|
| Elastic Modulus | 1.325 ± 0.2 MPa |
| Thickness | 0.29 ± 0.01 mm |
| Content Uniformity | 93% ± 10% |

The thickness of the film at different locations is measured at 0.29 mm with very small margin of variability which is an indication of the high uniformity of the film (Table 4). A maximum thickness variation of 5% is permitted in the preparation of the rapidly dissolving film. A uniform thickness across the film as it directly correlates with the accuracy of the dose in the film. Drug content in film is measured at 93%±10 indicating high level of consistency of epinephrine dose within the film (Table 2), as a limit of 8-115% of content uniformity is acceptable according to USP.

Figure 9:
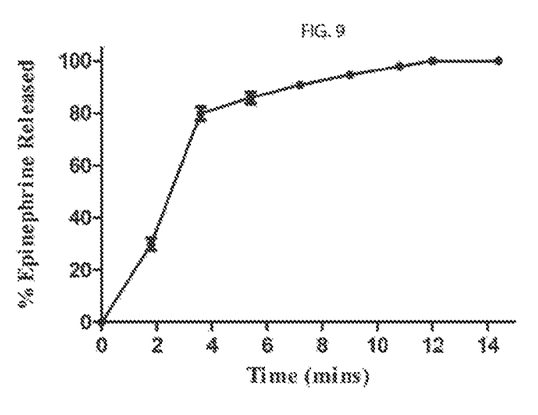
FIG. 9 shows a release profile of the epinephrine from the optimized fast dissolving film in 500 ml Simulated Saliva at 37° C.

Now referring to FIG. 9, the dissolution profile of epinephrine from the film in terms of rate and extent in simulated saliva is determined on six samples of the optimized film. More than 90% of epinephrine is released from the film within minutes.

Taste and disintegration time of the optimized film are evaluated on 6 volunteers (Table 3). The disintegration time is the time when the film starts to break or disintegrates. Volunteers reported 10-30 seconds disintegration time (Table 3). This complies with the regulations set by United State Pharmacopeia (USP) for disintegration time of oral films (not exceeding 30 seconds). Bitterness of epinephrine is masked efficiently according to volunteer's comments (Table 5). Four volunteers sensed no bitterness of the film while the other two volunteers reported slight to very slight sensation of bitterness. Moreover, no tongue constriction is reported by any of the volunteers. This data presents clear proof of the efficiency of rapidly dissolving film in taste masking the bitterness of epinephrine and an indication of strong potential for using a rapidly dissolving film as a replacement therapy of epinephrine injections for children.

TABLE 5

In vivo taste and disintegration time evaluation of the optimized epinephrine FDF.

| Volunteer | Bitterness | Tongue Constriction | Disintegration Time |
|---|---|---|---|
| 1 | None | None | ~10 seconds |
| 2 | None | None | ~10 seconds |
| 3 | Slight | None | ~20 seconds |
| 4 | None | None | ~30 seconds |
| 5 | Very slight | None | ~20 seconds |
| 6 | None | None | ~30 seconds |

Materials—Epinpherine hydrochloride, sodium metabisulfite, citric acid monohydrate and sodium citrate monobasic are purchased from Sigma Aldrich (St. Louis, Mo.). Lycoat® RS720 is obtained from Roquette (Lestrem, France). Glycerin and tween 80 are purchased from Fisher Chemicals (Pittsburg, Pa.). Xylitol is purchased from Gallipot (St. Paul, Minn.). Tutti Frutti is obtained from LorAnn Oils (Lansing, Mich.). Film Preparation—Several rapidly dissolving films are prepared by a solvent casting technique to choose the optimum film formulation. The formulation compositions of the rapidly dissolving film are mentioned in Table 3. LYCOAT and Xylitol are dissolved in warm water. The solution is then placed in a sonicator for two hours and then the solution is left overnight to ensure the removal of all entrapped air bubbles. Other excipients and Epinephrine HCl are added to the solution on the next day at room temperature. The mixture is then placed again in a sonicator for 40 minutes. The mixture is then spread onto a checkered paper covered by plastic sheet using a stainless-steel bar applicator. The film is left to dry overnight and is cut into 9 mm$^2$ small film strips.

Physical properties—The thickness and elastic modulus of the optimized film is evaluated using Dynamic Mechanical Analyzer (Q800 DMA, TA instruments, New Castle, Del.). This is important to evaluate tensile properties of the films. Three strips of the optimized films are tested at 25° C. according to ASTM International Test Method for Thin Plastic Sheeting (D 882-02). Each film is positioned between the grips of the instrument. The preload force is set at 0.01 N and the final force at 15 N. The initial grip separation is set to 60 mm and crosshead speed is set to 500 mm/min. The test is terminated when the film breaks. Elastic modulus is determined as the slope of the straight-line part of the stress-strain curve and it is expressed in force per unit area (MPa).

Drug content uniformity: Specific areas are cut from six different films and weighted to calculate the estimated amount of drug in each area. Films are then dissolved in 100 ml of citric acid buffer. The media are stirred and then filtered using 0.45 um filters (Millipore Corporation, Millipore, Vimodron, Italy) and epinephrine content is assessed using UVmini-1240 UV-Vis Spectrophotometer (Shimadzu, Japan) at wavelength 280 nm. Epinephrine content is determined by calculating the percentage of the measured epinephrine to the estimated amount in each film.

In vitro dissolution test: For the dissolution test, rapidly dissolving film are evaluated using USP dissolution apparatus II, paddle (Distek Evolution 6100, North Brunswick, N.J.). Six strips are placed in different 1 L vessels containing 500 ml Simulated Saliva. The temperature of the dissolution media is set to 37° C. and rpm is set to 50 rpm. Samples are taken at different time points throughout the time of the experiment (15 mins), and the amount of epinephrine released in the media is determined by UVmini-1240 UV-Vis Spectrophotometer (Shimadzu, Japan) at 280 nm.

Human taste panel—To evaluate the palatability of optimized epinephrine film, a taste evaluation study is performed on six healthy volunteers. The study is carried out in accordance with The Code of Ethics of the World Medical Association (Declaration of Helsinki), and all volunteers are informed in advance of the related details and the goal of the study and their consents are obtained. Volunteers are asked to place the film on the interior surface of their buccal cavity until the film is fully disintegrated. Volunteers then rinsed their mouths with drinking water. Volunteers have to report their findings of the presence of bitterness or not, any tongue restriction and how long it took for full disintegration of the film.

Equivalent elements can be substituted for the ones set forth above such that they perform in substantially the same manner in substantially the same way for achieving substantially the same result. It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

I claim:

1. A compound formulated as a pharmaceutical composition in a unit dosage form configured for sublingual or buccal administration of a Formula:

wherein R is selected from the group consisting of: —CHCH$_2$, —CHCHCH$_3$, —CH$_2$—CH$_2$—Cl, —CHCH$_2$I, —CH(Cl)CH$_2$ (Cl), —CH(I)CH$_2$(I), —CH(CH$_3$)CH$_2$(CH$_3$), —CH$_2$C(CH$_3$)$_3$, —CH$_2$CH$_2$CH$_3$, —CH$_2$Cl, —CH$_2$I, —CH$_2$F, H, Cl, I, F, —CH(CH$_3$)CH(CH$_3$)$_2$, —CH(Cl)CH (Cl)$_2$, —CH(I)CH(I)$_2$, —CH(F)CH(F)$_2$, —CH$_2$CHCH$_2$, —C(Cl)$_2$CH(Cl)$_2$, —C(I)$_2$CH(I)$_2$, —C(Cl)$_3$, C(I)$_3$, —CH$_2$COCH$_3$, —CH$_2$COCl, —CH$_2$CO(I), —CH$_2$OCH$_3$, —CH(I)(CH$_3$), —C(Cl)$_2$(CH$_3$), —CH$_2$CH(CH$_3$)$_2$, —CH$_2$CH(Cl)$_2$, —CH$_2$CH(I)$_2$, —CH$_2$C(Cl)$_3$, —CH$_2$C(I)$_3$, —CH(Cl)$_2$, —CH(I)$_2$, —C(CH$_3$)$_2$CH(CH$_3$)$_2$, —NH—C (CH$_3$) 3, —NH—CH(CH$_3$)$_2$, —NH—CH$_2$CH$_3$, —NH—CH$_3$, —SCH$_3$, —SCH$_2$CH$_3$, —SCH(CH$_3$)$_2$, —SC(CH$_3$)$_3$, —CH$_2$C$_6$H$_5$ and —C$_6$H$_5$ or a pharmaceutically acceptable salt thereof, wherein said compound has a Log P value in the range of about 0.5-6.0 and wherein the compound is formulated in a unit dosage form as a rapidly dissolving film and has a half-life $t_{1/2}$ range from 1-6 minutes.

2. A compound of a Formula wherein R is selected from the group consisting of: CH$_3$, CH$_2$CH$_3$ and CH(CH$_3$)$_2$ wherein the compound is formulated in a unit dosage form as a sublingual or buccal administration and wherein the compound is formulated in a unit dosage form as a rapidly dissolving film and has a half-life $t_{1/2}$ range from 1-6 minutes.

3. The compound of claim 2, wherein the compound is selected from the group consisting of: 4-(1-hydroxy-2-(methylamino)ethyl)-1,2-phenylene di-acetate; 4-(1-hydroxy-2(methylamino)ethyl)-1,2-phenylene bis(2-methylpropanoate); 4-(1-hydroxy-2-(methylamino)ethyl)-1,2-phenylene dipropanoate; and a pharmaceutically acceptable carrier or a pharmaceutically acceptable excipient, wherein the compound is formulated in a unit dosage form as a rapidly dissolving film.

4. A compound formulated as a pharmaceutical composition in a unit dosage form configured for sublingual or buccal administration of a Formula:

wherein R is comprised of —C(Cl)$_2$CH$_3$.

5. The composition of claim 4 wherein the compound is formulated in a unit dosage form as a rapidly dissolving film and has a half-life $t_{1/2}$ range from 1-6 minutes.

* * * * *